US011013807B2

(12) United States Patent
Mao et al.

(10) Patent No.: US 11,013,807 B2
(45) Date of Patent: May 25, 2021

(54) STABLE FAT-SOLUBLE ACTIVE INGREDIENT COMPOSITION, MICROCAPSULE AND PROCESS OF PREPARATION AND USE THEREOF

(71) Applicants: Zhejiang Medicine Co., Ltd. Xinchang Pharmaceutical Factory, Shaoxing (CN); ZheJiang Medicine Co., Ltd. Vitamin Factory, Shaoxing (CN)

(72) Inventors: Guoquan Mao, Shaoxing (CN); Hongming Zhu, Shaoxing (CN); Wenxin Ma, Shaoxing (CN); Zhiping Liang, Shaoxing (CN); Li Qian, Shaoxing (CN); Fritz Bernhard Lubbe, Shaoxing (CN); Siping Hu, Shaoxing (CN); Chun Li, Shaoxing (CN); Shanping Wen, Shaoxing (CN); Qinlan Wang, Shaoxin (CN); Huajuan Kong, Shaoxing (CN)

(73) Assignees: ZHEJIANG MEDICINE CO., LTD. XINCHANG PHARMACEUTICAL FACTORY, Shaoxing (CN); ZHEJIANG MEDICINE CO., LTD. VITAMIN FACTORY, Shaoxing (CN)

( * ) Notice: Subject to any disclaimer, the term of this patent is extended or adjusted under 35 U.S.C. 154(b) by 0 days.

(21) Appl. No.: 15/874,906

(22) Filed: Jan. 19, 2018

(65) Prior Publication Data

US 2018/0207277 A1   Jul. 26, 2018

(30) Foreign Application Priority Data

Jan. 20, 2017 (CN) .......................... 201710042526.X
Aug. 15, 2017 (CN) .......................... 201710694878.3

(51) Int. Cl.
| | | |
|---|---|---|
| A61K 47/22 | (2006.01) |
| A23K 20/174 | (2016.01) |
| A23L 2/52 | (2006.01) |
| A23L 33/15 | (2016.01) |
| A61K 31/01 | (2006.01) |
| A61K 31/12 | (2006.01) |
| A61K 31/23 | (2006.01) |
| A23L 3/3499 | (2006.01) |
| A23L 3/349 | (2006.01) |
| A23P 10/30 | (2016.01) |
| A23L 33/155 | (2016.01) |
| A23L 3/3544 | (2006.01) |
| A23K 40/30 | (2016.01) |
| A23D 7/005 | (2006.01) |
| A23K 20/147 | (2016.01) |
| A23D 7/00 | (2006.01) |

(Continued)

(52) U.S. Cl.
CPC .............. *A61K 47/22* (2013.01); *A23D 7/003* (2013.01); *A23D 7/0053* (2013.01); *A23D 7/02* (2013.01); *A23K 20/147* (2016.05); *A23K 20/158* (2016.05); *A23K 20/163* (2016.05); *A23K 20/174* (2016.05); *A23K 40/30* (2016.05); *A23L 2/52* (2013.01); *A23L 3/349* (2013.01); *A23L 3/3499* (2013.01); *A23L 3/3544* (2013.01); *A23L 33/15* (2016.08); *A23L 33/155* (2016.08); *A23P 10/30* (2016.08); *A61K 8/11* (2013.01); *A61K 8/31* (2013.01); *A61K 8/35* (2013.01); *A61K 8/355* (2013.01); *A61K 8/361* (2013.01); *A61K 8/37* (2013.01); *A61K 8/375* (2013.01); *A61K 8/4953* (2013.01); *A61K 8/55* (2013.01); *A61K 8/67* (2013.01); *A61K 8/671* (2013.01); *A61K 8/676* (2013.01); *A61K 8/678* (2013.01); *A61K 9/5089* (2013.01); *A61K 31/01* (2013.01); *A61K 31/07* (2013.01); *A61K 31/12* (2013.01); *A61K 31/122* (2013.01); *A61K 31/201* (2013.01); *A61K 31/202* (2013.01); *A61K 31/23* (2013.01); *A61K 31/231* (2013.01); *A61K 31/522* (2013.01); *A61K 31/593* (2013.01); *A61K 31/685* (2013.01); *A61Q 19/00* (2013.01); *A23V 2002/00* (2013.01); *A23V 2200/02* (2013.01); *A61K 2800/10* (2013.01); *A61K 2800/522* (2013.01)

(58) Field of Classification Search
CPC ........ A61K 47/22; A61K 8/671; A61K 8/676; A61K 8/678; A61K 8/67; A61K 31/01; A61K 31/12; A61K 8/11; A23K 20/163; A23D 7/0053; A23L 3/3499; A23L 2/52
See application file for complete search history.

(56) References Cited

U.S. PATENT DOCUMENTS

| | | | | |
|---|---|---|---|---|
| 6,117,419 A | * | 9/2000 | Vernice | .................. A61K 8/042 106/415 |
| 6,887,502 B2 | * | 5/2005 | Chen | ....................... A23P 10/30 426/602 |

(Continued)

FOREIGN PATENT DOCUMENTS

| | | | |
|---|---|---|---|
| CN | 102362864 | * | 3/2013 |
| CN | 102363864 | * | 3/2013 |

*Primary Examiner* — Mina Haghighatian
(74) *Attorney, Agent, or Firm* — Ashok Tankha

(57) ABSTRACT

The present invention provides a stable fat-soluble active ingredient composition, microcapsule and process for preparation and use thereof. The fat-soluble active ingredient composition comprises tocopherol, vitamin C palmitate and a fat-soluble active ingredient; wherein the weight ratio of tocopherol to vitamin C palmitate is 2-8:1, the weight ratio of a combination of tocopherol with vitamin C palmitate to the fat-soluble active ingredient is 7-13:100. The present invention obtains a novel antioxidant composition without hidden dangers for improving the stability of the fat-soluble active ingredient by screening a combination of antioxidants and adjusting their proportion and dose.

6 Claims, No Drawings

(51) Int. Cl.

| | |
|---|---|
| *A23K 20/163* | (2016.01) |
| *A61K 8/37* | (2006.01) |
| *A61K 31/593* | (2006.01) |
| *A61K 31/07* | (2006.01) |
| *A23D 7/02* | (2006.01) |
| *A23K 20/158* | (2016.01) |
| *A61K 31/201* | (2006.01) |
| *A61K 8/11* | (2006.01) |
| *A61K 8/31* | (2006.01) |
| *A61K 8/35* | (2006.01) |
| *A61K 8/36* | (2006.01) |
| *A61K 8/49* | (2006.01) |
| *A61K 8/55* | (2006.01) |
| *A61K 8/67* | (2006.01) |
| *A61K 9/50* | (2006.01) |
| *A61K 31/122* | (2006.01) |
| *A61K 31/202* | (2006.01) |
| *A61K 31/231* | (2006.01) |
| *A61K 31/522* | (2006.01) |
| *A61K 31/685* | (2006.01) |
| *A61Q 19/00* | (2006.01) |

(56) References Cited

U.S. PATENT DOCUMENTS

| | | | |
|---|---|---|---|
| 2007/0141211 A1* | 6/2007 | Kolar, Jr. | A61K 9/1617 426/302 |
| 2008/0207777 A1* | 8/2008 | Auweter | A23D 7/011 514/785 |
| 2008/0299209 A1* | 12/2008 | Beck | A61K 8/0241 424/490 |
| 2009/0041911 A1* | 2/2009 | Gamay | A23L 2/02 426/115 |
| 2011/0014288 A1* | 1/2011 | Hansen | A61K 9/50 424/484 |
| 2011/0207831 A1* | 8/2011 | Kopsel | A23D 7/0053 514/763 |
| 2012/0059070 A1* | 3/2012 | Elger | A61K 8/645 514/773 |

* cited by examiner

STABLE FAT-SOLUBLE ACTIVE INGREDIENT COMPOSITION, MICROCAPSULE AND PROCESS OF PREPARATION AND USE THEREOF

CROSS-REFERENCE TO RELATED APPLICATIONS

This application claims priority to and the benefit of Chinese patent application number 201710042526.X filed in the State Intellectual Property Office of the People's Republic of China on Jan. 20, 2017, and Chinese patent application number 201710694878.3 filed in the State Intellectual Property Office of the People's Republic of China on Aug. 15, 2017. The specifications of the above referenced patent applications are incorporated herein by reference in their entirety.

FIELD OF THE INVENTION

The present invention relates to a novel green antioxidant composition for increasing the stability of vitamin A ester. In particular, the present invention relates to a stable fat-soluble active ingredient composition, microcapsule and process of preparation and use thereof.

BACKGROUND OF THE INVENTION

Vitamins are necessary for animal nutrition and production and have a very important role on the body's metabolism, growth, development and health. Vitamin A is a very important member of the vitamin A ester family and has a very important function on visual health, bone health, reproduction and cell division and reproduction. It would be inconceivable for the lack of vitamin A in the human body.

Vitamin A is a light yellow crystalline solid, insoluble in water, and is soluble in fat and varieties of fat solvents, and is easy to deteriorates in the light, heat and oxygen, and then is easily destroyed. Therefore, it must firstly be esterified in the preparation of vitamin A additive. Generally it would be made into microcapsules powder for use.

As for a microencapsulation embedding technology, vitamin A ester as a core material is melted to form an oil phase, and then dissolved with high molecular material as wall material. Small molecule filler and emulsifier in water forms an aqueous phase. The oil phase and the aqueous phase are mixed, and then emulsified, sprayed drying or crosslinked, and finally to obtain a microcapsule product.

An antioxidant is added to prevent from oxidation of vitamin A esters in the preparation of vitamin A ester microcapsules of the above process. At present, antioxidants generally includes ethoxyquinoline, tert-butyl hydroxytoluene and butylated hydroxyanisole. But these antioxidants have a trend to be limited uses even prohibited uses in the international food and feed industry due to their associated potential hazards.

There are some green safe and healthy antioxidants such as tocopherol or vitamin C palmitate without hidden dangers of limiting or prohibiting uses in the food and feed industry. Tocopherol is a fat-soluble antioxidant for effectively preventing from the formation of active oxides during the oxidation of fat. It would be necessary for normal growth and fertility of animals. Vitamin C palmitate is a highly effective oxygen scavenger and synergist, and evaluated as a nutritious, non-toxic, efficient, safe use food additive by the World Health Organization (WHO) Food Additives Committee and is also the sole antioxidant available for infant food in China, and also used as an antioxidants and has some effects on food color protection, nutrition enhancement for foods.

Chinese Patent CN102362864 (B) introduces a method for enhancing free-running property and bulk density of vitamin A or vitamin D3 microcapsules, wherein the antioxidant is tocopherol or vitamin C palmitate.

Chinese Patent CN102176833 (A) introduces a preparation method of ready-to-use stable emulsion, wherein the antioxidant is tocopherol, t-butylhydroxytoluene, t-butylhydroxyanisole, ascorbic acid or ethoxyquinoline, wherein the emulsifier is ascorbyl palmitate (vitamin C palmitate).

Chinese Patent CN103181566 (A) describes powder preparation of vitamin A ester, wherein the water-soluble antioxidant may be ascorbic acid and its salts, such as sodium ascorbate and so on. And the fat-soluble antioxidant may be tocopherol; fatty acid ascorbate, such as ascorbyl palmitate or stearate; BHT; BHA; propyl gallate; ethoxyquinoline.

Chinese Patent CN1279112 (A) introduces a carbohydrate matrix comprising a composition of fat-soluble substances, wherein the antioxidant is selected from sodium ascorbate, palmitate of ascorbic acid, dl-tocopherol, mixed tocopherol, lecithin and their mixtures.

All of above patents mentioned antioxidants comprising tocopherol or vitamin C palmitate, but do not describe a combination of tocopherol with vitamin C palmitate, and do not describe a dose of use and a proportion of the antioxidants.

SUMMARY OF THE INVENTION

At present, antioxidants generally include ethoxyquinoline, tert-butyl hydroxytoluene and butylated hydroxyanisole. But these antioxidants have a trend to be limited uses even prohibited uses in the international food and feed industry due to their associated potential hazards.

The purpose of the present invention is to eliminate hidden dangers of limited uses of antioxidants such as ethoxyquinoline, t-butylhydroxytoluene and t-butylhydroxyanisole, and to overcome some deficiencies in the fat-soluble active ingredients such as vitamin A ester in microcapsule production. The present invention obtains a novel antioxidant composition without hidden dangers for the stability improvement of the fat-soluble active ingredient by screening a combination of antioxidants and adjusting their proportion and dose.

According to the first aspect of the present invention, the present invention provides a stable fat-soluble active ingredient composition, the fat-soluble active ingredient composition comprises tocopherol, vitamin C palmitate and a fat-soluble active ingredient; wherein the weight ratio of tocopherol to vitamin C palmitate is 2-8:1, the weight ratio of a combination of tocopherol with vitamin C palmitate to the fat-soluble active ingredient is 7-13:100.

In the technical solution of the fat-soluble active ingredient composition of the present invention, preferably, the stable fat-soluble active ingredient composition is any one of a combination of tocopherol and vitamin C palmitate, a combination of tocopherol and sodium ascorbate, as well as a combination of sodium ascorbate and vitamin C palmitate.

In the technical solution of the fat-soluble active ingredient composition of the present invention, preferably, wherein the weight ratio of tocopherol to vitamin C palmitate is 3-7:1.

In the technical solution of the fat-soluble active ingredient composition of the present invention, more preferably, the weight ratio of tocopherol to vitamin C palmitate is 4-6:1.

In the technical solution of the fat-soluble active ingredient composition of the present invention, preferably, the weight ratio of a combination of tocopherol with vitamin C palmitate to the fat-soluble active ingredient is 8-12:100.

In the technical solution of the fat-soluble active ingredient composition of the present invention, more preferably, the weight ratio of a combination of tocopherol with vitamin C palmitate to the fat-soluble active ingredient is 9-11:100.

In the technical solution of the fat-soluble active ingredient composition of the present invention, more preferably, tocopherol includes one or more of synthetic or natural $\alpha$-tocopherol, $\beta$-tocopherol, $\gamma$-tocopherol and $\delta$-tocopherol.

In the technical solution of the fat-soluble active ingredient composition of the present invention, preferably, the fat-soluble active ingredient is selected from the group consisting of vitamin A, vitamin D, vitamin K, carotenoid and polyunsaturated fatty acid or ester thereof. More preferably, the vitamin A is vitamin A ester. Most preferably, the vitamin A ester is vitamin A acetate, or vitamin A palmitate, or vitamin A propionate, or vitamin $AD_3$, or a mixture of the above substances, wherein the vitamin $AD_3$ is a mixture of vitamin A ester and vitamin $D_3$.

According to the second aspect of the present invention, the present invention further provides a fat-soluble active ingredient microcapsule containing the fat-soluble active ingredient composition.

According to the third aspect of the present invention, the present invention further provides an use of the fat-soluble active ingredient composition in the preparation of foods, beverages, animal feeds, cosmetics or pharmaceuticals.

According to the forth aspect of the present invention, the present invention further provides a process for preparing the fat-soluble active ingredient microcapsule, and the method comprises the following steps:

1) blending and melting a fat-soluble active ingredient with an antioxidant in a certain weight ratio at temperature of 45-85° C. under nitrogen protection to form an oil phase A of a fat-soluble active ingredient molten oil; wherein the antioxidant is tocopherol and vitamin C palmitate, the fat-soluble active ingredient is selected from the group consisting of vitamin A, vitamin D, vitamin K, coenzyme Q10, carotenoid and polyunsaturated fatty acid and ester thereof; 2) dissolving a gelatin or a modified starch as a low molecular filler and a glucose or a white sugar in water at 60-70° C. under nitrogen protection, to obtain an aqueous phase B; 3) blending the oil phase A of step 1) with the aqueous phase B of step 2) under nitrogen protection, and then high-speed shear emulsifying, degasifying and homogenizing under nitrogen protection in closed conditions, to obtain an emulsion; and 4) spraying granulation the emulsion of step 3), and then fluidizing drying, to obtain a fat-soluble active ingredient microcapsule.

In the technical solution of the process of the present invention, preferably, crosslinking the fat-soluble active ingredient microcapsule of step 4), to obtain a repelling water type fat-soluble active ingredient microcapsule.

In the technical solution of the process of the present invention, preferably, the weight ratio of the solution of the aqueous phase B is 30-50 wt %.

The term "the stability improvement" used in the present invention is referred to improve the stability of the fat-soluble active ingredient (selected from the group consisting of vitamin A, vitamin D, vitamin K, coenzyme Q10, carotenoid and polyunsaturated fatty acids or esters thereof) molten oil or emulsion or microcapsule by adding the antioxidant (tocopherol and vitamin C palmitate) in the present invention. That is, the antioxidant (such as tocopherol and vitamin C palmitate) can efficiently delay the oxidation of the fat-soluble active ingredient and can increase the antioxidant effect. It can be evaluated by the following simple method.

The polyunsaturated fatty acids or esters thereof in the present invention is referred to as a linear polyunsaturated fatty acid of C12-25 or its acetate, glyceride, phosphate; preferably, linoleic acid, linolenic acid, EPA, or DHA.

The fat-soluble active ingredient molten oil is placed in a sample bottle and sealed from light, storied at 40° C., and then respectively detected its content in 0, 2, 4, 6 days. Its content retention rate is greater than 96% after 6 days.

The fat-soluble active ingredient emulsion is placed in a sample bottle and sealed from light, storied at 40° C., and then respectively detected its content in 0, 1, 2, 3 weeks. Its content retention rate is greater than 95% after 3 weeks.

The fat-soluble active ingredient microcapsule is placed in a sample bottle and sealed from light, storied at 40° C., and then respectively detected its content in 0, 2, 4, 6 weeks. Its content retention rate is greater than 94% after 6 weeks.

The term "screening", "adjusting" used in experiment method of the present invention is to find the optimal combination of antioxidants by an orthogonal experiment.

The orthogonal experiment method conducts an overall design, comprehensive comparison and statistical analysis for the experiment by a table in alignment (such as an orthogonal table) to find out better production conditions by several experiment times to achieve the highest production process effects. The orthogonal experiment method firstly selects an orthogonal table corresponding to experiment factors. It shall start with doing experiment based on the table after establishing an experiment table, and then processing those datum. Processing data is a very important step because number of trials is greatly reduced. Analyzing data is firstly to find out the best data from all of the experiment data. Of course, the data is certainly not the best match data, but it is closest to the best match data. Afterwards, summing the same level experiment data of each factor up obtains a table of experiment result of each level. It may obtain a group of the optimal factor from the table. And then it may obtain a changing trend of these factors by comparing with former factors in order to guide next experiment. Conducting a calculation such as range and variance among different levels experiment values in each factor learns a sensitivity of the factor. Then it shall make sure next experiment and narrow the scope of the experiment and finally determine an optimal value according to statistical data.

In the technical solution of process of preparing the fat-soluble active ingredient composition of the present invention, the weight ratio of combination of tocopherol with vitamin C palmitate to the fat-soluble active ingredient is 5-13:100, preferably 7-13:100. In the technical solution of process of preparing the fat-soluble active ingredient composition of the present invention, the weight ratio of tocopherol to vitamin C palmitate, the weight ratio of tocopherol to sodium ascorbate and the weight ratio of vitamin C palmitate to sodium ascorbate is respectively 1: 1-1:10, respectively, preferably 2-8:1.

The advantages of the present invention are as follows: 1) the antioxidants of the present invention are safe, green and healthy food additives, and can eliminate hidden dangers of limited uses of antioxidants such as ethoxyquinoline, tert-butyl hydroxytoluene and butylated hydroxyanisole; 2) the present invention obtains a novel antioxidant composition without hidden dangers for the stability improvement of the fat-soluble active ingredient (such as vitamin A ester) by screening a combination of antioxidants and adjusting their proportion and dose.

DETAILED DESCRIPTION OF THE INVENTION AND PREFERRED EMBODIMENTS THEREOF

Hereafter, the present invention will be described specifically with reference to the examples. The examples are given only for illustration of the technical solution of the present invention and should not be construed to limit the present invention.

Example 1

Vitamin A ester crystal, vitamin C palmitate and α-tocopherol are blended and melted at 75° C. under nitrogen protection to form a vitamin A molten oil. Factor level setting table of Table 1 and Orthogonal experiment schedule of Table 1 are determined based on weights of vitamin A ester crystal, vitamin C palmitate and α-tocopherol. The vitamin A ester molten oil is placed in a sample bottle and sealed from light, and stored at 40° C., and respectively detected its content in 0, 2, 4, 6 days.

TABLE 1

Factor Level Setting Table

| level | Factor (ratio) | |
|---|---|---|
| | Vitamin C palmitate A | α-tocopherol B |
| 1 | 1% | 6% |
| 2 | 1.5% | 8% |
| 3 | 2% | 10% |

Note:
The percentage value of Table 1 is the weigh ratio of antioxidant to vitamin A.

TABLE 2

Orthogonal experiment schedule

| NO. | Experiment factors | |
|---|---|---|
| | A | B |
| 1 | 1 | 1 |
| 2 | 1 | 2 |
| 3 | 1 | 3 |
| 4 | 2 | 2 |
| 5 | 2 | 3 |
| 6 | 2 | 1 |
| 7 | 3 | 3 |
| 8 | 3 | 1 |
| 9 | 3 | 2 |

Analyzing results of 2, 4, 6 days respectively, conducting a comprehensive judgment as a final experiment result, and conducting a range analysis on a content retention, and selecting a primary and secondary relation and excellent combination.

TABLE 3

Orthogonal Experiment Analysis Table of Content Retention Rate

| NO. | Experiment factors | | Content retention rate | | |
|---|---|---|---|---|---|
| | A | B | 2 days | 4 days | 6 days |
| 1 | 1 | 1 | 98.80% | 96.10% | 95.50% |
| 2 | 1 | 2 | 99.00% | 98.20% | 97.50% |
| 3 | 1 | 3 | 98.40% | 96.50% | 96.10% |
| 4 | 2 | 2 | 98.80% | 97.90% | 97.00% |
| 5 | 2 | 3 | 98.00% | 96.50% | 95.50% |
| 6 | 2 | 1 | 99.20% | 98.00% | 97.50% |
| 7 | 3 | 3 | 98.80% | 97.20% | 97.00% |
| 8 | 3 | 1 | 99.10% | 98.10% | 97.50% |
| 9 | 3 | 2 | 99.80% | 98.30% | 97.60% |
| content retention rate in 2 days | k1 | 0.987 | 0.990 | Comprehensive judgment: Primary and secondary B > A Excellent combination A3B2 | | |
| | k2 | 0.987 | 0.992 | | | |
| | k3 | 0.992 | 0.984 | | | |
| | R | 0.006 | 0.008 | | | |
| | Primary and secondary | B > A | | | | |
| | Excellent combination | A3B2 | | | | |
| content retention rate in 4 days | k1 | 0.969 | 0.974 | | | |
| | k2 | 0.975 | 0.981 | | | |
| | k3 | 0.979 | 0.967 | | | |
| | R | 0.009 | 0.014 | | | |
| | Primary and secondary | B > A | | | | |
| | Excellent combination | A3B2 | | | | |
| content retention rate in 6 days | k1 | 0.964 | 0.968 | | | |
| | k2 | 0.967 | 0.974 | | | |
| | k3 | 0.974 | 0.962 | | | |
| | R | 0.010 | 0.012 | | | |
| | Primary and secondary | B > A | | | | |
| | Excellent combination | A3B2 | | | | |

It may be seen from the Orthogonal experiment table of Table 2 and Table 3 that affecting the stability of vitamin A content is mainly tocopherol, is secondly vitamin C palmitate. According to the comprehensive judgment, the excellent combination is A3B2, namely, 2% vitamin C palmitate and 8% α-tocopherol.

Example 2

Vitamin A palmitate, vitamin C palmitate and β-tocopherol are blended and melted at 65° C. under nitrogen protection to form vitamin A palmitate molten oil. Gelatin and glucose are dissolved in water at 65° C. to form a gelatin and glucose aqueous phase solution. The vitamin A palmitate molten oil is poured into the gelatin and glucose aqueous phase solution and then emulsified under high-speed shear condition, degassed and homogenized, to obtain a stable emulsion. The stable emulsion (that is, vitamin A palmitate emulsion) is placed in a sample bottle and sealed from light, stored at 40° C., and respectively detected its content in 0, 1, 2, 3 weeks. Data of content retention rates of different antioxidant ratio emulsion are listed in the Table 4.

TABLE 4

Statistical Table of Content Retention Rate of Vitamin A Palmitate Emulsion of Different Antioxidant Combination

| NO. | β-tocopherol | Vitamin C palmitate | Content retention rates of Vitamin A palmitate | | | |
|---|---|---|---|---|---|---|
| | | | 0 week | 1 week | 2 weeks | 3 weeks |
| 1 | 2.0% | 0.0% | 100% | 92.5% | 90.0% | 86.1% |
| 2 | 4.0% | 0.0% | 100% | 92.2% | 89.8% | 86.5% |
| 3 | 6.0% | 0.0% | 100% | 92.9% | 89.7% | 87.5% |
| 4 | 8.0% | 0.0% | 100% | 93.0% | 90.2% | 88.2% |
| 5 | 10.0% | 0.0% | 100% | 93.1% | 90.1% | 89.5% |
| 6 | 0.0% | 0.5% | 100% | 92.6% | 89.6% | 85.8% |
| 7 | 0.0% | 1.0% | 100% | 92.8% | 88.9% | 85.9% |
| 8 | 0.0% | 1.5% | 100% | 92.7% | 89.5% | 86.5% |
| 9 | 0.0% | 2.0% | 100% | 93.0% | 89.6% | 86.8% |
| 10 | 0.0% | 2.5% | 100% | 92.8% | 89.4% | 86.6% |
| 11 | 5.0% | 2.5% | 100% | 97.2% | 94.8% | 92.8% |
| 12 | 6.0% | 2.0% | 100% | 97.6% | 95.9% | 93.6% |
| 13 | 8.0% | 2.0% | 100% | 98.5% | 96.8% | 95.2% |
| 14 | 10.0% | 2.0% | 100% | 98.4% | 96.9% | 95.3% |
| 15 | 9.6% | 1.6% | 100% | 98.3% | 96.7% | 95.1% |
| 16 | 10.0% | 1.4% | 100% | 97.8% | 96.2% | 94.2% |
| 17 | 10.0% | 1.2% | 100% | 97.5% | 95.8% | 93.3% |

It may be obviously seen from datum of Table 4 that the content retention rate of the vitamin A palmitate emulsion is higher in the range of formula ratio of the present invention.

Example 3

50 kg of vitamin A acetate crystal and 0.5 kg of vitamin C palmitate and 3.5 kg of synthetic tocopherol are blended and melted at 85° C. under nitrogen protection to form a vitamin A acetate molten oil. 75 kg of gelatin and 50 kg of glucose are dissolved in 130 kg of water at 60° C., to form a 49% gelatin and glucose aqueous phase solution.

The vitamin A acetate molten oil is poured into the 49% gelatin and glucose aqueous phase solution and emulsified under high-speed shear condition, and then degassed and homogenized to obtain a stable emulsion; and then the stable emulsion is delivered into a starch bed to conduct a pray granulation, and then fluidized dried and crosslinked under high temperature to obtain 218 kg of water-repellent vitamin A acetate microcapsule. The content of vitamin A acetate is 520,000 IU/g and the microencapsulated yield is 95%, by the HPLC analysis. The vitamin A ester microcapsule is placed in a sample bottle and sealed from light, stored at 40° C. for 6 weeks, and the content of vitamin A ester is 490,000 IU/g, and the content retention rate is 94.2%.

Example 4

50 kg of coenzyme Q10 crystal and 0.5 kg of vitamin C palmitate and 3 kg of natural γ-tocopherol are blended and melted at 45° C. under nitrogen protection to form a coenzyme Q10 oil. 75 kg of gelatin and 50 kg of glucose are dissolved in 130 kg of water at 70° C., to form a 49% gelatin and glucose aqueous phase solution.

The coenzyme Q10 oil is poured into the 49% gelatin and glucose aqueous phase solution and emulsified under high-speed shear condition, and then degassed and homogenized to obtain a stable emulsion, and then the stable emulsion is delivered into a starch bed to conduct a pray granulation, and then fluidized dried and crosslinked under high temperature to obtain 218 kg of water-repellent coenzyme Q10 microcapsule. The content of coenzyme Q10 is 52% and the microencapsulated yield is 95%, by the HPLC analysis. The coenzyme Q10 microcapsules are placed in a sample bottle and sealed away from light, stored at 40° C. for 6 weeks, and the content of coenzyme Q10 is 49%, and the content retention rate is 94.2%.

Examples 5-11

The experiment method is the same as that of Example 1. Preparing different fat-soluble active ingredient oil and the retention rate is determined in the Table 5.

TABLE 5

| Example | Fat-soluble active ingredient | Tocopherol | | VC palmitate | Retention rate of fat-soluble active ingredient | | | |
|---|---|---|---|---|---|---|---|---|
| | | Type | Weight ratio | | 0 week | 1 week | 2 weeks | 3 weeks |
| 5 | Vitamin K | α | 5.0% | 2.5% | 100% | 98.3% | 97.6% | 97.0% |
| 6 | Xanthin | β | 6.0% | 2.0% | 100% | 98.6% | 97.9% | 97.0% |
| 7 | Astaxanthin | γ | 8.0% | 2.0% | 100% | 98.7% | 97.8% | 96.5% |
| 8 | Lycopene | Synthetic | 10.0% | 2.0% | 100% | 98.1% | 96.5% | 95.1% |
| 9 | DHA Acetate | Natural | 9.6% | 1.6% | 100% | 98.5% | 97.8% | 96.3% |
| 10 | Linoleic acid glyceride | Mixed | 10.0% | 1.4% | 100% | 97.8% | 96.6% | 96.4% |
| 11 | Linolenic acid phosphate | Mixed | 10.0% | 1.2% | 100% | 98.0% | 96.3% | 95.2% |

It may be obviously seen from Table 5 that the content retention rate of the fat-soluble active ingredient is higher in the range of formula ratio of the present invention.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A fat-soluble active ingredient microcapsule, comprising a stable fat-soluble active ingredient composition for increasing stability of a fat-soluble active ingredient, said stable fat-soluble active ingredient composition comprising tocopherol, vitamin C palmitate and a fat-soluble active ingredient, wherein the weight ratio of tocopherol to vitamin C palmitate is 2-8:1, the weight ratio of a combination of tocopherol with vitamin C palmitate to the fat-soluble active ingredient is 7-13:100, wherein the fat-soluble active ingredient is selected from the group consisting of docosahexaenoic acid acetate, linoleic acid glyceride, and linolenic acid phosphate.

2. The fat-soluble active ingredient microcapsule according to claim 1, wherein the weight ratio of tocopherol to vitamin C palmitate is 3-7:1.

3. The fat-soluble active ingredient microcapsule according to claim 2, wherein the weight ratio of tocopherol to vitamin C palmitate is 4-6:1.

4. The fat-soluble active ingredient microcapsule according to claim 1, wherein the weight ratio of a combination of tocopherol with vitamin C palmitate to the fat-soluble active ingredient is 8-12:100.

5. The fat-soluble active ingredient microcapsule according to claim 4, wherein the weight ratio of the combination of tocopherol with vitamin C palmitate to the fat-soluble active ingredient is 9-11:100.

6. The fat-soluble active ingredient microcapsule according to claim 1, wherein the stable fat-soluble active ingredient composition is used in the preparation of foods, beverages, animal feeds, cosmetics or pharmaceuticals.

* * * * *